(12) United States Patent
Biedermann et al.

(10) Patent No.: US 9,750,543 B2
(45) Date of Patent: Sep. 5, 2017

(54) ANCHORING MEMBER SUITABLE FOR USE IN A POLYAXIAL BONE ANCHORING DEVICE AND POLYAXIAL BONE ANCHORING DEVICE WITH AN ENLARGED PIVOT ANGLE TO ONE SIDE

(71) Applicant: Biedermann Technologies GmbH & Co. KG, Donaueschingen (DE)

(72) Inventors: Lutz Biedermann, VS-Villingen (DE); Wilfried Matthis, Weisweil (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 0 days.

(21) Appl. No.: 14/099,625

(22) Filed: Dec. 6, 2013

(65) Prior Publication Data

US 2014/0188174 A1    Jul. 3, 2014

Related U.S. Application Data

(60) Provisional application No. 61/735,307, filed on Dec. 10, 2012.

(30) Foreign Application Priority Data

Dec. 10, 2012    (EP) .................................... 12196376

(51) Int. Cl.
*A61B 17/70*    (2006.01)
*A61B 17/88*    (2006.01)
(Continued)

(52) U.S. Cl.
CPC ...... *A61B 17/7037* (2013.01); *A61B 17/7035* (2013.01); *A61B 17/8605* (2013.01);
(Continued)

(58) Field of Classification Search
CPC ... A61B 17/70; A61B 17/8605–17/866; A61B 17/7001; A61B 17/7032–17/7046
(Continued)

(56) References Cited

U.S. PATENT DOCUMENTS

| 5,545,228 A | 8/1996 | Kambin |
| 6,736,820 B2 | 5/2004 | Biedermann et al. |

(Continued)

FOREIGN PATENT DOCUMENTS

| JP | 11-019881 A | 1/1999 |
| JP | 2001340348 A | 12/2001 |

OTHER PUBLICATIONS

Extended European Search Report for European Application No. 12196376.3, European Search Report dated May 22, 2013 and mailed May 31, 2013 (10 pgs.).
(Continued)

*Primary Examiner* — Jacqueline Johanas
(74) *Attorney, Agent, or Firm* — Lewis Roca Rothgerber Christie LLP

(57) ABSTRACT

An anchoring member for a polyaxial bone anchoring device includes a bone anchoring section having a first end, a second end, a core having a first portion with a constant cross-sectional area, and a bone engagement structure on at least a portion of the core, a head, wherein a central axis extends through respective centers of the head and the first and second ends of the bone anchoring section, and a neck, the neck having an outer surface that is asymmetric with respect to the central axis, wherein a first cross-section of the neck perpendicular to the central axis includes a portion of the neck where the outer surface of the neck is at a minimum distance from the central axis, wherein a cross-sectional area of the first cross-section of the neck is at least the cross-sectional area of the first portion of the core of the bone anchoring section.

24 Claims, 6 Drawing Sheets

(51) Int. Cl.
*A61B 17/86* (2006.01)
*A61B 17/00* (2006.01)

(52) U.S. Cl.
CPC ...... *A61B 17/8615* (2013.01); *A61B 17/8625* (2013.01); *A61B 17/888* (2013.01); *A61B 2017/00455* (2013.01)

(58) Field of Classification Search
USPC .................................................. 606/246–279
See application file for complete search history.

(56) References Cited

U.S. PATENT DOCUMENTS

| | | | |
|---|---|---|---|
| 7,485,132 B1 | 2/2009 | McBride et al. | |
| D642,270 S * | 7/2011 | McAfee | D24/155 |
| 8,029,539 B2 * | 10/2011 | Kirschman | 606/246 |
| 2002/0058942 A1 | 5/2002 | Biedermann et al. | |
| 2003/0171755 A1 * | 9/2003 | Moseley et al. | 606/73 |
| 2005/0015097 A1 | 1/2005 | Mujwid et al. | |
| 2005/0043735 A1 | 2/2005 | Ahmad | |
| 2010/0160977 A1 * | 6/2010 | Gephart et al. | 606/305 |
| 2010/0312280 A1 * | 12/2010 | Overes et al. | 606/264 |
| 2011/0125265 A1 * | 5/2011 | Bagga et al. | 623/16.11 |
| 2011/0172719 A1 | 7/2011 | Gorhan et al. | |
| 2013/0281995 A1 * | 10/2013 | Saunders et al. | 606/20 |
| 2014/0148853 A1 * | 5/2014 | Smith | 606/246 |

OTHER PUBLICATIONS

Partial European Search Report for European Application No. 12196376.3, European Search Report dated Apr. 9, 2013 and mailed Apr. 17, 2013 (5 pgs.).

Japanese Office action for Application No. 2013-251838, dated Oct. 25, 2016, including English translation, 12 pages.

* cited by examiner

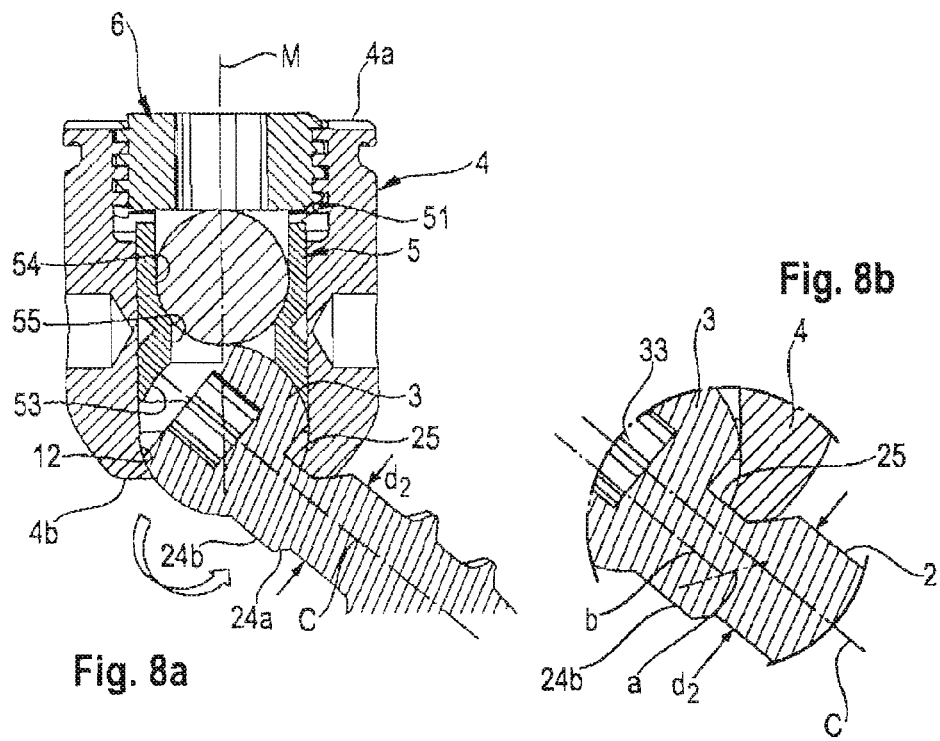
Fig. 8a
Fig. 8b
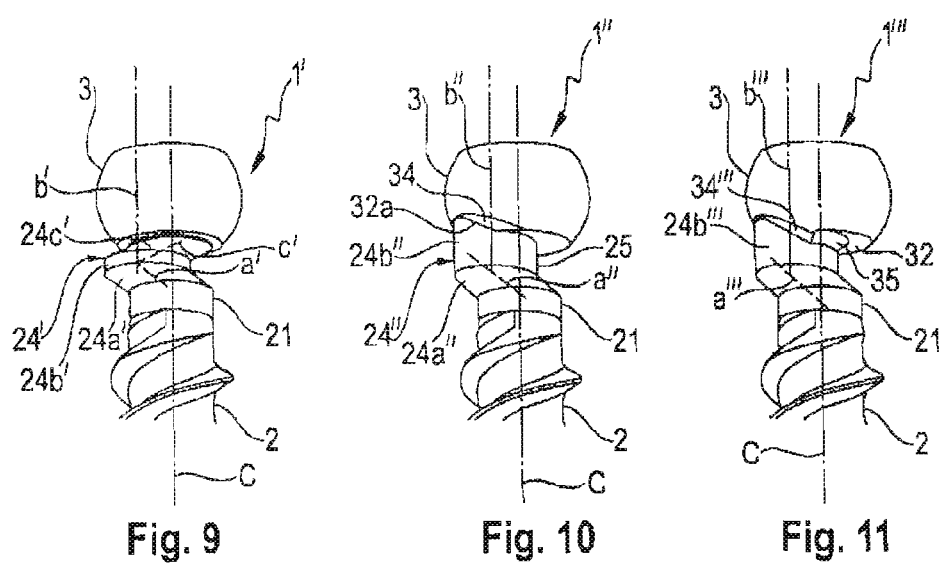
Fig. 9
Fig. 10
Fig. 11

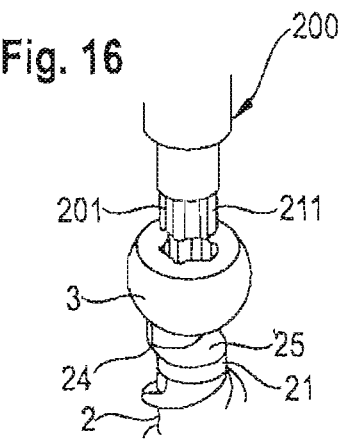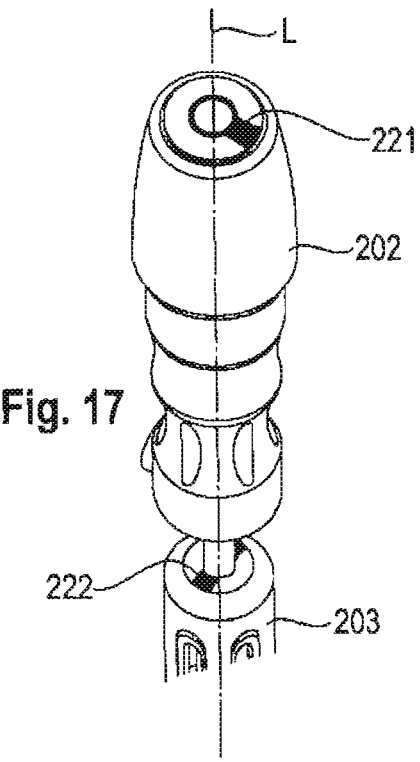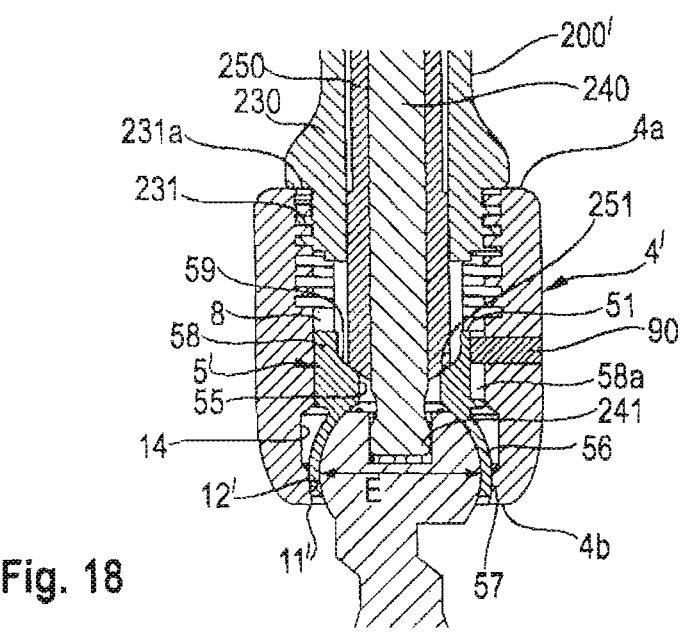

ANCHORING MEMBER SUITABLE FOR USE IN A POLYAXIAL BONE ANCHORING DEVICE AND POLYAXIAL BONE ANCHORING DEVICE WITH AN ENLARGED PIVOT ANGLE TO ONE SIDE

CROSS-REFERENCE TO RELATED APPLICATION(S)

The present application claims priority to and the benefit of U.S. Provisional Patent Application Ser. No. 61/735,307, filed Dec. 10, 2012, the contents of which are hereby incorporated by reference in their entirety, and claims priority from European Patent Application EP 12 196 376.3, filed Dec. 10, 2012, the contents of which are hereby incorporated by reference in their entirety.

BACKGROUND

Field

The invention relates to an anchoring member suitable for use in a polyaxial bone anchoring device and to a polyaxial bone anchoring device with a pivot angle that is enlarged to one side. The anchoring member includes a bone anchoring section and a head with a common central axis, and a neck portion between the bone anchoring section and the head, wherein the neck portion is asymmetric with respect to the central axis. The asymmetry of the neck portion is established by a recess that is present at one side of the neck portion and an extension or projecting portion that is present at an opposite side of the neck portion. A polyaxial bone anchoring device including such an anchoring member permits pivoting of the anchoring member to at least one side with an enlarged pivot angle.

Description of Related Art

A bone anchoring device with an enlarged pivot angle to one side is described in U.S. Pat. No. 6,736,820. The bone anchoring device includes a bone screw and a receiving part with an open first bore and a substantially U-shaped cross-section for receiving the rod and a second bore on the end opposite to the first bore and a seat for the head. In one embodiment, the screw member has a neck between a head and a threaded section, the neck having a recess or countersink and being asymmetric with respect to the symmetry axis. As a result thereof, the screw member can pivot at a larger angle to the side where the recess or countersink is present.

Another bone anchoring device with increased angulation is known from U.S. Pat. No. 8,029,539 B2. It includes a screw having a head, a shank and an intermediate or neck portion. The neck portion comprises a first surface or area having a relatively large radius and a second surface or area that has a relatively small radius. The larger and smaller radiuses of the surfaces permit the retainer of the anchoring device to be pivoted at a plurality of different angles or degrees.

SUMMARY

It is an object of the invention to provide an improved anchoring member suitable for use in a polyaxial bone anchoring device with an enlarged pivot angle to one side, and to a polyaxial bone anchoring device that has an increased strength with respect to loads acting on it. Furthermore, an instrument for use with the polyaxial bone anchoring device may be provided.

A neck portion of the bone anchoring member is offset from a central axis extending through a head and a shank of the bone anchoring member. Therefore, a polyaxial bone anchoring device including a receiving part and the bone anchoring member permits pivoting of the bone anchoring member relative to the receiving part in a first direction at a first angle and in a second direction at a second angle, wherein the second angle is greater than the first angle. The enlarged pivot angle may be as much as 55° measured from the central axis, for example. An engagement portion for an instrument is provided on the head and the drive axis is coaxial with the central axis.

The bone anchoring member can be used with any known receiving part that is configured to pivotably receive a bone anchoring member. Hence, existing polyaxial bone anchoring devices can be modified into polyaxial bone anchoring devices with an enlarged pivot angle to one side by only exchanging anchoring members. This contributes to a reduction of costs.

Because an overall thickness of the neck portion of the bone anchoring member is not reduced substantially, the strength and safety of the polyaxial bone anchoring device under loads is not diminished compared to a polyaxial bone anchoring device with a reduced thickness of the neck portion.

An alignment feature may be provided on the bone anchoring member that allows pre-alignment of the bone anchoring member relative to the receiving part with respect to the orientation of the enlarged pivot angle.

An instrument adapted to be used with the polyaxial bone anchoring device can indicate the orientation or direction of the enlarged pivot angle relative to the receiving part even if the anchoring member is already inserted into the bone.

BRIEF DESCRIPTION OF DRAWINGS

Further features and advantages will be become apparent from the description of embodiments by means of the accompanying drawings. In the drawings:

FIG. 5b shows an enlarged view of an upper portion of the bone anchoring member of FIG. 5a;

FIG. 7 shows a top view of the bone anchoring member of FIG. 5a;

FIG. 8a shows a cross-sectional view of the polyaxial bone anchoring device according to the first embodiment, the cross-section taken along line A-A of the receiving part shown in FIG. 3;

FIG. 8b shows an enlarged view of a lower right portion of FIG. 8a;

FIG. 9 shows an enlarged perspective view of an upper portion of a bone anchoring member according to a second embodiment;

FIG. 10 shows an enlarged perspective view of an upper portion of a bone anchoring member according to a third embodiment;

FIG. 11 shows an enlarged perspective view of an upper portion of a bone anchoring member according to a fourth embodiment;

FIG. 16 shows an enlarged perspective view of a portion of the bone anchoring member with a front portion of an instrument for aligning the bone anchoring member with respect to the receiving part according to a first embodiment;

FIG. 17 shows a perspective view of a rearward portion of the instrument shown in FIG. 16;

FIG. 18 shows a cross-sectional view of a modified polyaxial bone anchoring device with a front portion of a second embodiment of an instrument;

DETAILED DESCRIPTION

Figure 1:
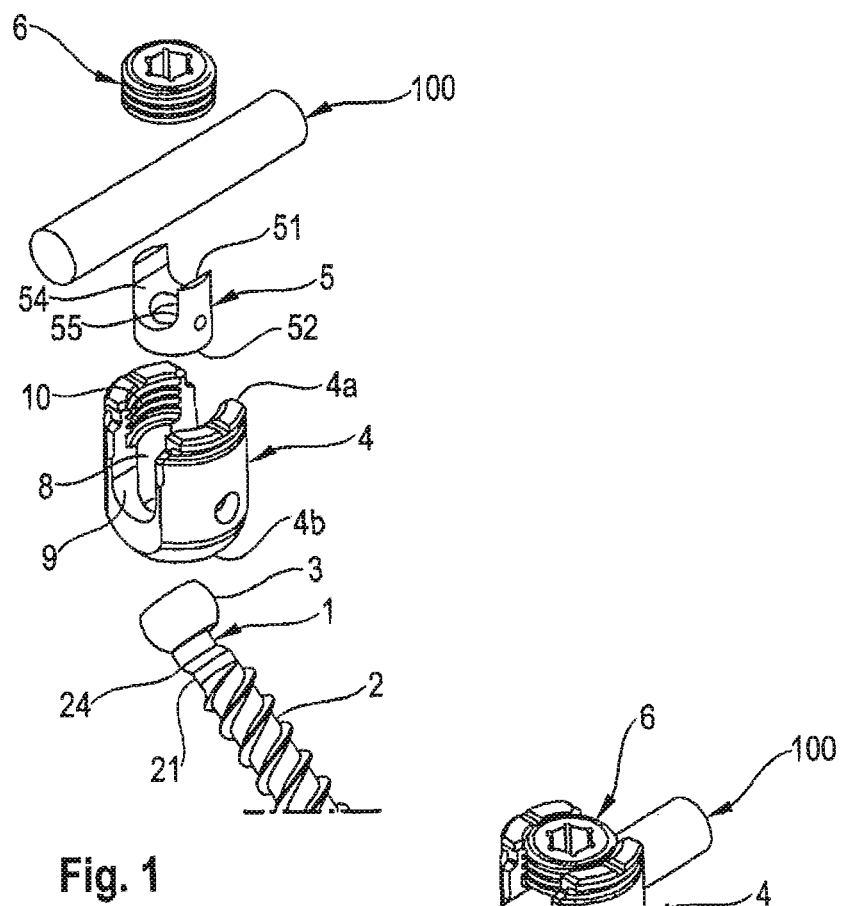
FIG. 1 shows an exploded perspective view of a polyaxial bone anchoring device according to a first embodiment.
Figure 2:
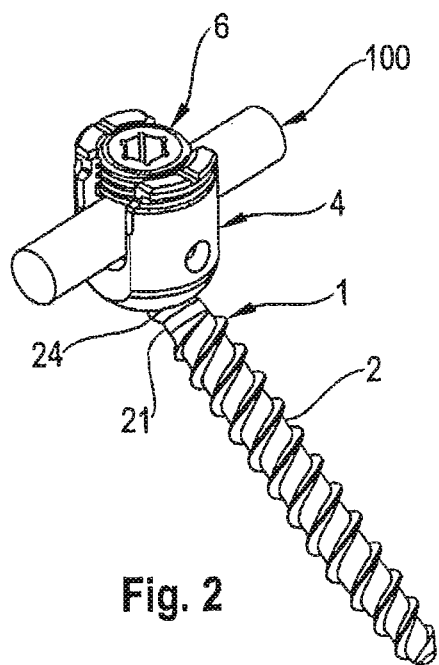
FIG. 2 shows a perspective view of the polyaxial bone anchoring device of FIG. 1 in an assembled state.

Referring to FIGS. 1 and 2, a polyaxial bone anchoring device according to a first embodiment includes a bone anchoring member 1 including a shank 2 for anchoring in a bone or a vertebra and a head 3. Further, a receiving part 4 for pivotably receiving the head 3 of the bone anchoring member 1 is provided that is configured to couple the bone anchoring member 1 to a stabilization rod 100. A pressure member 5 may be provided to exert pressure onto the head 3 in the receiving part 4 to lock the head 3 in a specific angular position with respect to the receiving part 4. Furthermore, a locking member 6 in the form of a set screw may be provided for securing and fixing the rod 100 in the receiving part 4.

Figure 3:
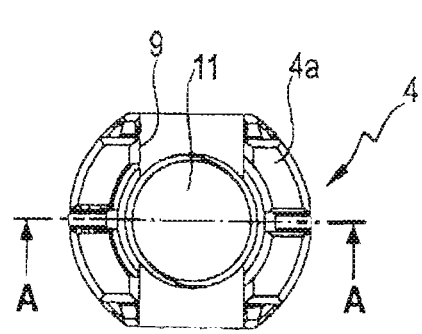
FIG. 3 shows a top view of a receiving part of the polyaxial bone anchoring device according to the first embodiment.
Figure 4:
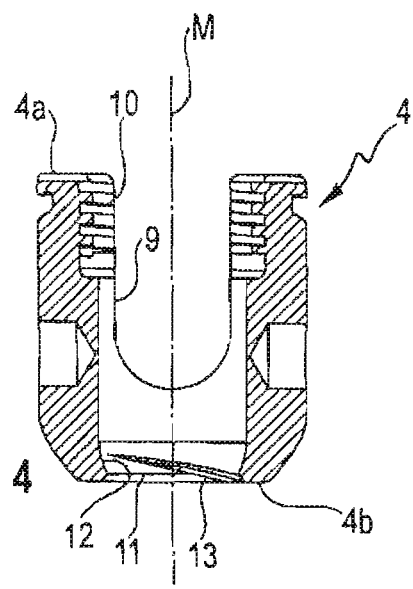
FIG. 4 shows a cross-sectional view of the receiving part of FIG. 3, the cross-section taken along line A-A in FIG. 3.
Figure 5A:
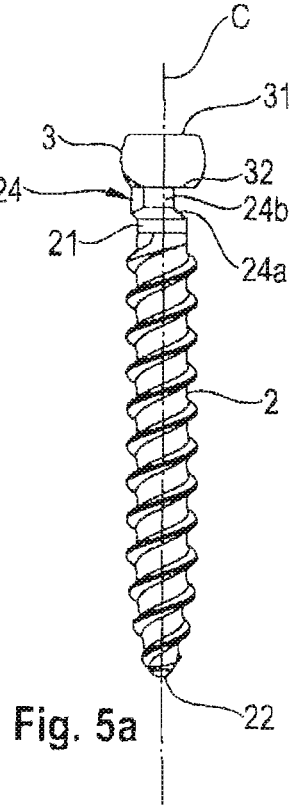
FIG. 5a shows a side view of a bone anchoring member according to the first embodiment.
Figure 5B:
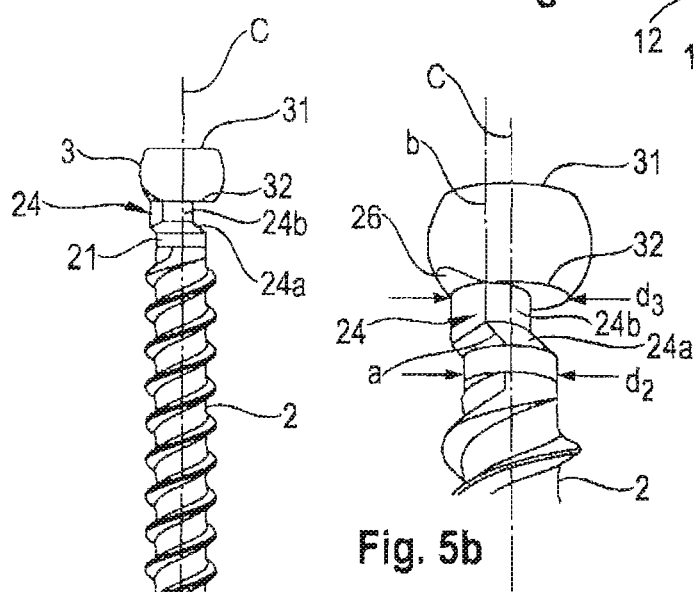
Figure 6:
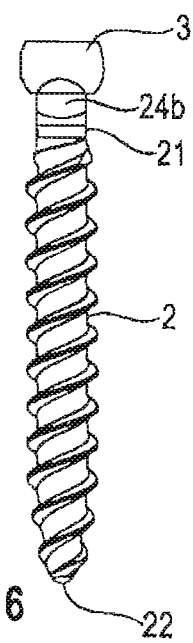
FIG. 6 shows a side view of the bone anchoring member of FIG. 5a, rotated by 90°.
Figure 7:
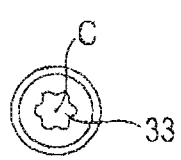

Referring more in detail to FIGS. 3 and 4, the receiving part 4 has a top end 4a and a bottom end 4b, an axis of symmetry M and a coaxial bore 8 (see FIG. 1) extending from the top end 4a in the direction of the bottom end 4b. Adjacent to the top end 4a, a substantially U-shaped recess 9 is provided that serves as a channel for receiving the rod 100. By means of the recess 9, two free legs are formed which are provided with an internal thread 10 for cooperating with the locking member 6.

The passage provided by the coaxial bore 8 narrows towards the second end 4b and an opening 11 is provided whose inner diameter is of such a size that the bone anchoring member can be guided through with its shank 2 until the head 3 is seated in a seat portion 12 adjacent to the opening 11. A portion 13 of a thread, for example, one turn of a thread may be provided in the seat portion 12 that permits the shank 2 to be screwed through the seat portion 12. This allows the use of relatively large bone anchoring members 1 without having to increase the dimensions of the seat 12 and of the lower opening 11 too much.

Referring now to FIGS. 5a to 7, the bone anchoring member 1 has a central axis C extending through the head 3 and the shank 2. The head 3 is substantially spherical segment-shaped and has a free end surface 31 and a bottom surface 32 opposite the free end surface 31. At the free end surface 31, an engagement portion for an instrument in the form of a recess 33 is provided. A maximum diameter $d_3$ of the bottom surface 32 of the head 3 is smaller than a corresponding maximum diameter of the free end surface 31.

The shank 2 has a first end 21 facing the head 3 and an opposite second end 22 that may be shaped as a tip. On at least a portion of the outer surface of the shank 2, a bone engagement structure in the form of a bone thread is provided. In a region adjacent to the first end 21, the shank has a maximum outer diameter $d_2$ and is symmetrical around the central axis C. The outer diameter $d_2$ may be the same as the core diameter of the bone thread. Between the first end 21 of the shank 2 and the bottom surface 32 of the head 3, a neck portion 24 is provided that connects the shank 2 to the head 3. The neck portion 24 is asymmetric with respect to the central axis, meaning that a central axis going through at least one section of the neck portion 24 does not coincide or is not coaxial with the central axis C through the head 3 and the shank 2. More specifically, in the first embodiment, the neck portion 24 has a first inclined section 24a having substantially the same outer diameter as the outer diameter $d_2$ of the end portion 21 of the shank. A central axis a of the first section 24a extends at an angle with respect to the central axis C. Between the first section 24a and the bottom surface 32 of the head 3 is a second upright section 24b that has a central axis b extending substantially parallel to the central axis C. As can be seen in particular in FIG. 8b, the first inclined section 24a is shorter than the second upright section 24b. Hence, the first inclined section 24a facilitates for providing the second upright section 24b at a position offset from the central axis C.

Referring to FIGS. 8a and 8b, the offset of the central axis b of the second upright portion 24b provides a recessed area 25 between the bottom surface 32 of the head 3 and the first end 21 of the shank 2 that permits larger angulation in the direction of the recessed area as explained below.

On a side opposite to the recessed area 25, the second upright section 24b has an extension in a radial direction that goes beyond the outer diameter $d_2$ of the end portion 21 of the shank 2 (see FIGS. 8a and 8b). Therefore, a total thickness in a radial direction of the second upright neck portion 24b is not substantially reduced when compared to a neck portion that has only a recess or a countersink. The whole neck portion 24 may be manufactured, for example, by providing a cylindrical neck portion between the head 3 and the shank 2 that has a greater outer diameter compared to the end portion 21 of the shank 2, and then removing a portion thereof at one side.

The pressure member 5 will now be described, referring to FIGS. 1 and 8a. The pressure member 5 is formed as a monolithic piece. It is of substantially cylindrical construction and has an outer diameter that allows it to move in an axial direction within the bore 8 of the receiving part 4. The pressure member 5 has a top end 51 and a bottom end 52. At the bottom end 52, a substantially spherical recess 53 is provided that is adapted to the size of the head 3. At the top end 51, a substantially U-shaped recess 54 is formed that is configured to receive the rod 100 therein. In this embodiment, the surface of the rod 100 extends above the side walls of the recess 54 when the rod 100 is inserted into the recess 54. More specifically, it may be advantageous in some embodiments if the side walls of arms defining the recess 54 extend to a height slightly below a height corresponding to the diameter of the rod 100 when the rod 100 is inserted. Furthermore, the pressure member 5 has a coaxial bore 55 for allowing access to the head 3 of the anchoring member 1 with an instrument (not shown).

The locking member 6 is a set screw that can be screwed between legs of the receiving part 4. The locking member 6 is configured to contact the rod 100 when the rod 100 is inserted into the receiving part 4.

The parts of the polyaxial bone anchoring device are preferably made from a biocompatible material, in particular from a biocompatible metal or a metal alloy, such as titanium, stainless steel, from Ni—Ti alloys such as Nitinol, or from a biocompatible plastic material, such as, for example, polyether ether ketone (PEEK). The parts may be all made of the same or of different materials.

The polyaxial bone anchoring device may be pre-assembled, with the bone anchoring member 1 being inserted from the top end 4a into the receiving part 4 until the head 3 presses in the seat 12. When the shank 2 is passed through the lower opening 11, the bone thread may engage the portion 13 of a thread turn, so that the shank 2 can be screwed through the lower opening 11. The pressure member 5 may be rotationally fixed within the receiving part 4, for example, by crimping. In the pre-assembled state, the pressure member 5 may exert a pre-load onto the head 3 to preliminarily hold the head 3 in a specific angular position by friction.

In use, at least two bone anchoring members 1 with receiving parts 4 are inserted into bone or in adjacent vertebrae, and are connected by the rod 100. Referring in particular to FIGS. 8a and 8b, the bone anchoring member 1 is permitted to pivot due to its recessed area 25 at the neck portion 24 at an angle to the right side (as illustrated) that is greater than an angle to the left side with respect to the axis of symmetry M of the receiving part 4.

A second embodiment of the bone anchoring member is shown in FIG. 9. The bone anchoring member 1' includes a neck portion 24' that is different from the neck portion 24 of the bone anchoring member 1 of the previous embodiment. The neck portion 24' has a first section 24a', a central axis a' which is angled with respect to the central axis C of the bone anchoring member 1', followed by a second section 24b' that is substantially cylindrical and a central axis b' which is parallel to the central axis C of the bone anchoring member 1', further followed by a third section 24c' with a central axis c' that is angled with respect to the central axis C in an opposite or otherwise different direction when compared to the central axis a'. The second portion 24b' extends beyond the end portion 21 of the shank 2 at one side. An area of the neck portion 24' of the cross-section in any plane perpendicular to the central axis C of the bone anchoring member 1' is substantially the same. In particular, an outer diameter of the second section 24b' is substantially the same as the outer diameter $d_2$ of the end portion 21 of the shank 2. Therefore, the strength of the neck portion 24' which has the offset section 24b' is substantially the same as that of a conventional bone anchoring member with a neck portion coaxial to the central axis C and that has a diameter corresponding to that of the end portion 21 of the shank 2.

A third embodiment of the bone anchoring member is shown in FIG. 10. The bone anchoring member 1" has a neck portion 24" that has a first cylindrical inclined section 24a" with a central axis a" extending at an angle to the central axis C, and a second upright cylindrical section 24b" with a central axis b" extending parallel to the central axis C. Hence, the second section 24b" extends beyond the end portion 21 of the neck 2 at one side and the neck portion 24" has a recessed area 25 on an opposite side. The second upright section 24b" goes over or continues partially into the head 3 with a slanted surface 32a that provides enhanced stability. Also in this embodiment, an area of cross section in any plane perpendicular to the central axis C is substantially the same. In addition, the bone anchoring member 1" according to this embodiment may have slanted transition portions 34 between head 3 and the second section 24b" of the neck portion 24" to facilitate pivoting of the head 3 in the receiving part 4.

A fourth embodiment of the bone anchoring member is shown in FIG. 11. The bone anchoring member 1''' differs from the bone anchoring member 1" in that the slanted transition portions 34''' are narrower. In addition, a substantially rounded cutout portion 35 is provided at the transition between the second neck section 24b''' and the bottom side 32 of the head 3. Hence, the pivoting movement of the head 3 in the seat 12 of the receiving part 4 is further facilitated. The rounded cutout portion 35 may further increase the strength of the bone anchoring element under load due to the avoidance of an edge at the connection between the neck portion 24''' and the head 3.

Figure 12:
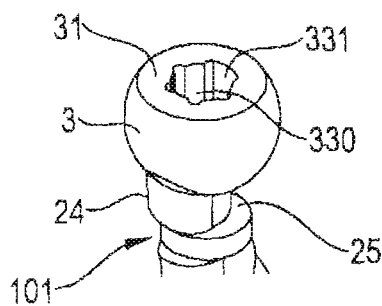
FIG. 12 shows a perspective view from the top of an upper portion of a modified bone anchoring member that has an alignment feature.

A further modified first embodiment of the bone anchoring member is shown in FIG. 12. The bone anchoring member 101 is identical to the bone anchoring member 1 according to the first embodiment, except for the design of the instrument engagement portion at the free end 31 of the head 3. The bone anchoring member 101 has an engagement portion 330 for an instrument at the free end surface 31 of the head 3, wherein the engagement portion 330 has an alignment feature 331 that is located at a position corresponding to the recessed region 25 between the shank 2 and the head 3 to more easily indicate or identify the position of the enlarged pivot angle. The alignment feature 331 may have an enlarged portion of a torx-shaped recess at one side. It shall be noted that the modified recess 330 can also be used in the embodiments shown in FIGS. 9 to 11.

Figure 13:
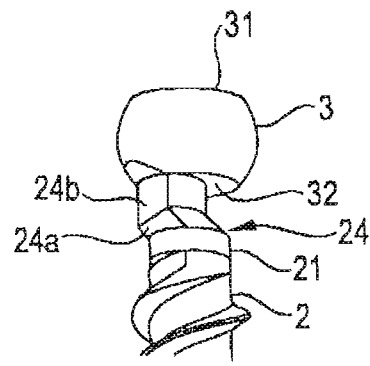
FIG. 13 shows a perspective view of an upper portion of a bone anchoring member according to an embodiment with a further example of an alignment feature.

Referring to FIG. 13, an alignment feature can also be realized through the shape of the neck portion 24 itself. Because at least a portion of the neck portion 24 of the bone anchoring member 1 extends through the lower opening 11, the shape of the neck portion 24 with the offset section 24b provides an alignment feature itself, to allow for easier alignment of the enlarged pivot angle.

Figure 14:
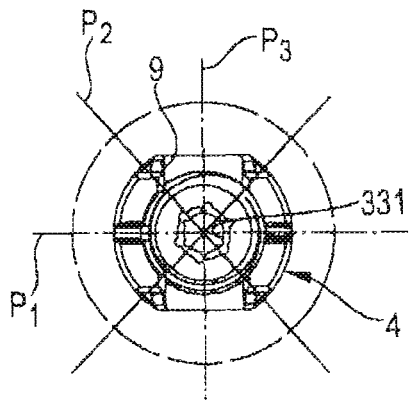
FIG. 14 shows a top view of a pre-assembled polyaxial bone anchoring device according to the first embodiment with the bone anchoring member pre-aligned.
Figure 15:
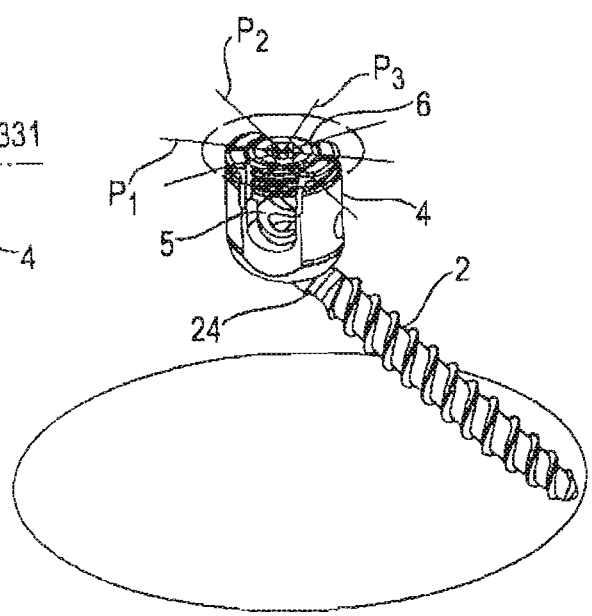
FIG. 15 shows a perspective view of the pre-assembled bone anchoring device with the pre-aligned bone anchoring member.

In a first method of use, the bone anchoring device is delivered in a pre-assembled form, wherein the shank 2 may be aligned in a pre-defined plane $p_1$ out of a plurality of planes $p_2$, $p_3$, etc., that contain the central axis M of the receiving part 4. As shown in FIG. 14, by means of the alignment feature 331 of the instrument engagement recess 330, the enlarged pivot angle is in the plane $p_1$ that extends perpendicular to the rod receiving recess 9. This plane may be pre-fixed by means of the locking member 6 pressing onto the pressure member 5, thereby locking the head 3 in the receiving part 4. For that purpose, it may be advantageous if the side walls of the pressure member 5 extend higher so that they can be more easily engaged by the locking element 6. The surgeon may then insert the bone anchoring device into the bone. The pre-defined orientation of the plane that includes the enlarged pivot angle can be maintained by friction force exerted onto the head 3 via the pre-fixed pressure member 5.

Alternatively, a pre-alignment can be achieved by rotating the bone anchoring member 1 so that, by means of the shape of the neck 24, the plane containing the enlarged pivot angle can be selected. With both methods, among others, pre-assembled, pre-aligned polyaxial bone anchoring devices can be delivered.

Referring to FIGS. 16 and 17, a first embodiment of an instrument 200 for inserting the bone anchoring member 1 includes a drive portion with a longitudinal axis L. The drive portion includes a front portion 201 that is configured to engage the recess 330. To achieve this, the front portion 201 has a torx-shape with a broadened section 211 that fits into the portion 331 of the recess 330. An end portion 202 opposite to the front portion 201 of the instrument includes a handle and an indication mark 221 at the free end surface of the handle that is visible to a user. The indication mark 221 may be colored or engraved, and may be a stripe or an engraved section, that has an orientation corresponding to the location of the broadened section 211 of the front portion 201. Hence, when the front portion 201 engages the recess 330 the indication mark 221 indicates the position of the broadened portion 211 of the front portion, and therefore also indicates a position of the recessed region 25 between the bottom side 32 of the head 3 and the shank 2. As a result, a user can more easily see the orientation of the plane with the enlarged pivot angle by means of the position of the indication mark 221.

The instrument 200 may further include a holding portion 203 that can be connected to the receiving part 4. At an upper surface of the holding portion 203 an indication mark 222, such as a colored stripe or an engraved portion, is provided indicating the orientation of the rod 100 or recess 9. The drive portion is rotatable with respect to the holding portion 203. Thus, when screwing in the bone anchoring member 1 with the drive portion, the indication mark 221 indicates the orientation of the recessed area 25 of the anchoring element 101 relative to the orientation of the rod 100 or recess 9 that is indicated by the indication mark 222.

In a second method of use, the bone anchoring member 1 is screwed into a bone part or a vertebra using the instrument 200 that engages the recess 330. The indication mark 222 indicates the orientation of the rod 100 or how the rod 100 will be positioned when inserted. The indication mark 221 indicates the position of the bone anchoring member 1 with respect to the receiving part 4, and therefore the orientation of the enlarged pivot angle with respect to the rod 100.

FIG. 18 shows a second embodiment of a polyaxial bone anchoring device and a second embodiment of an instrument. The polyaxial bone anchoring device differs with respect to the receiving part and the pressure member. Parts and portions that have the same reference numerals will not be repeated. The receiving part 4' allows insertion of the bone anchoring member 1 from the bottom end 4b. To achieve this, an opening 11' at the bottom end 4b is larger than a largest outer diameter of the head 3, so that the head 3 can be inserted through the opening 11'. Adjacent to the lower opening 11', there is a narrowing seat portion 12' that may be conically-shaped. Following the seat portion 12', there is an accommodation space 14 for accommodating the head 3 and a portion of the pressure member 5'. The pressure member 5' includes a lower cap-like portion 56 that can encompass the head 3 from the free-end of the head 3 to a position below the equator E of the head 3, i.e., the portion of the head 3 with the largest diameter. The lower cap-like portion 56 may be flexible, for example, by means of slits. The cap-like portion 56 has at its lower end an outer tapered section 57 that cooperates with the seat portion 12'. An upper portion 58 of the pressure member 5' is cylindrically shaped and has an outer diameter that permits movement within the bore 8. Preferably, at one side an elongate recess 58a is provided in the upper portion 58 of the pressure member 5' that can be engaged by a pin 90 extending through the wall of the receiving part 4' into the recess 58a and limiting an upward movement of the pressure member 5' in the direction of the top end 4a. The pressure member 5' has a substantially V-shaped recess 59 adjacent to its top end 51 that opens into a coaxial bore 55 in the center of the pressure member 5' and permits insertion of rods of different diameters.

The bone anchoring device according to the second embodiment is usually delivered as a pre-assembled device, including the receiving part 4' and the pressure member 5'. The device can be combined with the bone anchoring member 1, 1', 1", 1'" according to one of the previously described embodiments by inserting the head 3 through the lower opening 11' until the cap-like lower portion 56 snaps onto the head 3. The head 3 can be locked by moving the pressure member 5' downwards until the tapered section of the seat portion 12' and the outer tapered section 57 of the lower cap-like portion 56 of the pressure member 5' engage and clamp the head 3 therein. Before final locking of the head 3, the head 3 is pivotable in the lower cap-like portion 56 of the pressure member 5'.

An instrument 200' according to the second embodiment includes an outer tube-like portion 230, having a front end 231 with an external thread cooperating with the internal thread 10 of the receiving part 4'. The front portion 231 has a surface 231a that abuts against the top end 4a of the receiving part 4' to limit the insertion of the outer tube-like portion 230 therein.

The instrument 200' further includes a central post 240 with a front end 241 including an engagement portion, similar to the engagement portion 201 of the instrument 200, that has an asymmetry to fit into the recess 330 of the head 3 of the bone anchoring member 1. At an opposite end 242 of the central post 240, there is an indication mark 243 at a position corresponding to the alignment feature of the front portion 241 of the central post 240. The indication mark 243 indicates the position of the alignment feature at the front end 241. A tubular member 250 is provided around the central post 240 and inside the outer tube-like portion 230 of the instrument 200'. A front end 251 of the tubular member 250 abuts against the essentially V-shaped recess 59 of the pressure member 5'. An opposite end 252 of the tubular member 250 has a flat end surface with an indication mark 253 in the form of, for example a longitudinal stripe extending across the end surface 252. The indication mark 253 indicates a position of the rod receiving channel 59 in the pressure member 5' and the orientation of the U-shaped recess 9 in the receiving part 4'. The end surface 252 further has a central opening through which the end surface 242 of central post 240 can extend. Furthermore, a handle 232 connected to the outer tube-like portion 230 may be provided. The central post 240 and the outer tubular member 250 are rotatable with respect of the outer tube-like portion 230 of the instrument 200'.

Figure 19:
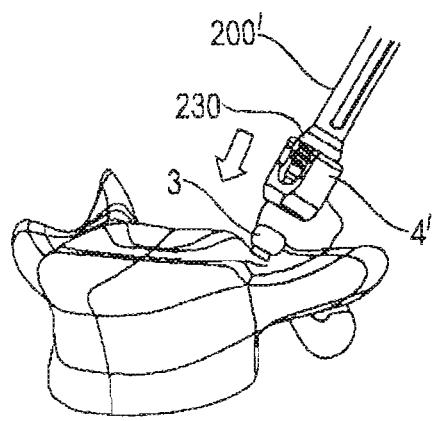
FIG. 19 shows a perspective view of a step of in-situ assembling of the polyaxial bone anchoring device of FIG. 18 with the instrument.
Figure 20:
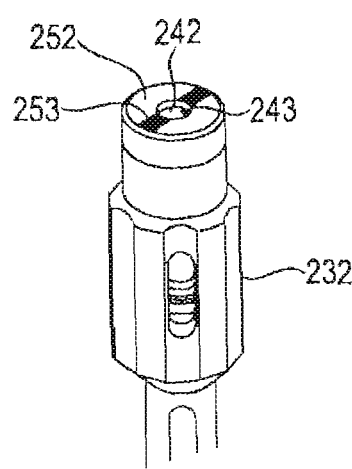
FIG. 20 shows a perspective view of an upper portion of the instrument shown in FIGS. 18 and 19 in a first configuration.
Figure 21:
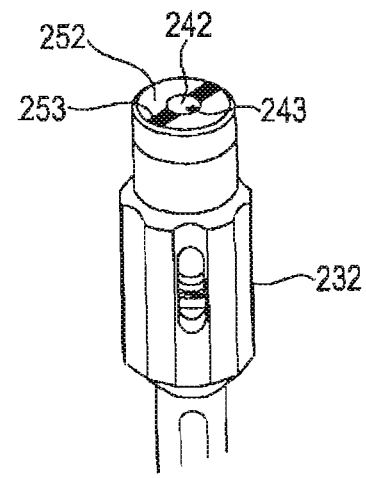
FIG. 21 shows a perspective view of an upper portion of the instrument of FIG. 20 in a second configuration.

In a third method of use, first, the bone anchoring member 1 is inserted into, for example, a pedicle of a vertebra as shown in FIG. 19. Then, the assembly including the receiving part 4' with pre-assembled pressure member 5' is connected to the tool 200' by screwing the outer tubular portion 230 into the receiving part 4'. Thereafter, the assembly is connected to the head 3 of the bone anchoring member 1 by inserting the head 3 into the receiving part 4', and more specifically into the lower cap-like portion 56 of the pressure member 5'. The outer tubular member 250 abuts against the recess 59 of the pressure member 5' when the pressure member 5' is correctly mounted. The indication mark 253 indicates the orientation of the rod to be inserted later. The indication mark 243 at the free end 242 of the central post 240 indicates the orientation of the enlarged pivot angle relative to the rod orientation. The dimensions of the parts of the instrument 200' are such that the free-end surface 242 of the central post 240 is flush with the free-end surface 252 when the receiving part 4' is correctly placed onto the head 3 (see, e.g., FIG. 21). Therefore, with the two indication marks 243, 253, the orientation of the enlarged pivot angle with respect to the orientation of the rod 100 or the recess 9 can be more easily identified in the case of a polyaxial bone anchoring device of the bottom loading type.

Modifications of the above embodiments are also possible. For the bone engagement structure of the shank 2, all kinds of bone engagement structures may be conceivable, such as barbs, a roughened surface, other kinds of bone threads, etc. Cannulated screws may also be used. An end portion of the shank adjacent to the neck portion may have a non-circular cross-section, for example, it may have a square or rectangular cross-section. The offset neck portion then extends beyond such a contour at a side opposite to the recessed area 25.

For the receiving part, all kinds of known receiving parts that allow a pivoting of a bone anchoring member in a seat provided in the receiving part or in a pressure member can also be used. Such a receiving part can be configured to couple the bone anchoring member to a rod. Alternatively, the receiving part can be provided in a bone plate.

A variety of known locking elements, including two part locking devices, may also be used.

The features of the different embodiments may also be combined among each other.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. An anchoring member for a polyaxial bone anchoring device, the anchoring member comprising:
 a bone anchoring section having a first end, a second end, and a bone engagement structure on at least a portion thereof;
 a head, wherein a central axis extends through respective centers of the head and the first and second ends of the bone anchoring section; and
 a neck between the bone anchoring section and the head, the neck having an outer surface that is asymmetric with respect to the central axis, wherein a first cross-section of the neck that is perpendicular to the central axis includes a portion of the neck where the outer surface of the neck is at a minimum distance from the central axis, the minimum distance being oriented in a first radial direction perpendicular to the central axis;
 wherein for a first portion of the neck located between the head and the first cross-section, a distance between the central axis and the outer surface in the first radial direction decreases as the neck extends along the central axis towards the first cross-section, while a distance between the central axis and the outer surface in a radial direction that is different from the first radial direction stays the same or increases as the neck extends along the central axis towards the first cross-section.

2. The anchoring member of claim 1, wherein the neck has at least one section with two ends, and wherein an axis extending through the two ends is substantially parallel to the central axis.

3. The anchoring member of claim 1, wherein the neck has at least one section with two ends, and wherein an axis extending through the two ends is at an angle relative to the central axis.

4. The anchoring member of claim 1, wherein the neck has two sections each having two ends and an axis extending through the two ends, wherein the respective axes of the two sections of the neck are at angles relative to the central axis.

5. The anchoring member of claim 4, wherein the angles of the respective axes of the two sections of the neck are oriented opposite to one another relative to the central axis.

6. The anchoring member of claim 5, wherein at least a portion of the neck adjacent to the head is aligned with the central axis.

7. The anchoring member of claim 1, wherein the bone engagement structure is a bone thread, wherein a core of the bone anchoring section defines a root of the bone thread, and wherein at least some of the neck extends farther from the central axis than the core extends from the central axis.

8. The anchoring member of claim 1, wherein at least two cross-sectional areas of the neck perpendicular to the central axis are substantially the same as one another.

9. The anchoring member of claim 1, wherein the head is spherical segment shaped.

10. The anchoring member of claim 1, wherein the head comprises a flattened or rounded transition surface at a side facing the neck.

11. The anchoring member of claim 1, wherein the central axis is coaxial with a drive axis or axis of rotation of the anchoring member, and wherein the head has an engagement portion for engagement with an instrument.

12. The anchoring member of claim 1, wherein the anchoring member comprises an alignment feature for identifying an orientation of the first radial direction.

13. The anchoring member of claim 12, wherein the alignment feature comprises a recess for an instrument.

14. The anchoring member of claim 13, wherein the recess is at a free end surface of the head.

15. An instrument for use with claim 13, wherein the recess is asymmetric, and wherein the instrument has a first portion with an asymmetric engagement portion configured to fit into the asymmetric recess of the anchoring member, and a second portion with a mark for identifying an orientation of the asymmetric engagement portion.

16. The anchoring member of claim 13, wherein
 the recess is an asymmetric torx-shaped recess having an enlarged recessed portion at one side formed by enlarging the portion of the recess between two adjacent points of the torx profile.

17. The anchoring member of claim 12, wherein the alignment feature comprises a shape of the neck.

18. A polyaxial bone anchoring device comprising:
 the anchoring member of claim 1; and
 a receiving part having an axis of symmetry and configured to pivotably receive the anchoring member;
 wherein the anchoring device is configured to pivot the anchoring member relative to the receiving part in the first radial direction at a first maximum angle, and to pivot the anchoring member relative to the receiving part in a second radial direction at a second maximum angle that is less than the first maximum angle.

19. The polyaxial bone anchoring device of claim 18, further comprising a pressure member configured to exert pressure on the head in the receiving part.

20. An instrument for use with the polyaxial bone anchoring device of claim 18, wherein the anchoring member has an asymmetric recess for engagement with the instrument, and the instrument has a first portion with an asymmetric engagement portion configured to fit into the recess and a second portion with a mark for identifying an orientation of the asymmetric engagement portion.

21. The anchoring member of claim 1, wherein a vector that is normal to at least one part of the neck or to a part of the head adjacent to the neck is parallel to the central axis.

22. A method for coupling a rod to a bone via a polyaxial bone anchoring device comprising a receiving part, a locking element, and an anchoring member configured to be pivotably connected to the receiving part, the anchoring member comprising a bone anchoring section having a first end, a second end, and a bone engagement structure on at least a portion thereof, a head, wherein a central axis extends through respective centers of the head and the first and second ends of the bone anchoring section, and a neck between the bone anchoring section and the head, the neck having an outer surface that is asymmetric with respect to the central axis, wherein a first cross-section of the neck that is perpendicular to the central axis includes a portion of the neck where the outer surface of the neck is at a minimum distance from the central axis, the minimum distance being oriented in a first radial direction perpendicular to the central axis, wherein for a first portion of the neck located between the head and the first cross-section, a distance between the central axis and the outer surface in the first radial direction decreases as the neck extends along the central axis towards the first cross-section, while a distance between the central axis and the outer surface in a radial direction that is different from the first radial direction stays the same or increases as the neck extends along the central axis towards the first cross-section, the method comprising:
  inserting the anchoring member into a bone;
  adjusting an angular position of the receiving part relative to the anchoring member;
  inserting a rod into a channel of the receiving part; and
  advancing the locking element in the receiving part to lock the angular position of the anchoring member and a position of the rod relative to the receiving part.

23. The method of claim 22, further comprising adjusting a rotational position of the anchoring member relative to the bone to align the first radial direction corresponding to a position of the minimum distance of the outer surface of the neck from the central axis with a direction of the adjustment of the angular position of the receiving part relative to the anchoring member.

24. The method of claim 22, further comprising connecting the anchoring member and the receiving part.

* * * * *

UNITED STATES PATENT AND TRADEMARK OFFICE
CERTIFICATE OF CORRECTION

PATENT NO. : 9,750,543 B2  
APPLICATION NO. : 14/099625  
DATED : September 5, 2017  
INVENTOR(S) : Lutz Biedermann et al.

Page 1 of 1

It is certified that error appears in the above-identified patent and that said Letters Patent is hereby corrected as shown below:

In the Claims

Column 10, Line 48, Claim 15    Delete "with claim 13"  
Insert --with the anchoring member of claim 13--

Signed and Sealed this  
Thirtieth Day of October, 2018

Andrei Iancu  
*Director of the United States Patent and Trademark Office*